United States Patent

Kubota

[11] 4,299,230
[45] Nov. 10, 1981

[54] STABBING APPARATUS FOR DIAGNOSIS OF LIVING BODY

[75] Inventor: Tetsumaru Kubota, Hachioji, Japan

[73] Assignee: Olympus Optical Co., Ltd., Tokyo, Japan

[21] Appl. No.: 37,352

[22] Filed: May 9, 1979

[51] Int. Cl.³ ............................................... A61B 5/00
[52] U.S. Cl. .................................. 128/630; 128/347; 128/329 R; 128/748
[58] Field of Search ................... 128/630, 347, 329 R, 128/748; 116/307

[56] References Cited

U.S. PATENT DOCUMENTS

| | | | |
|---|---|---|---|
| 4,154,228 | 5/1979 | Feldstein et al. | 128/329 R |
| 4,186,750 | 2/1980 | Patel | 128/347 X |
| 4,215,699 | 8/1980 | Patel | 128/347 X |

FOREIGN PATENT DOCUMENTS 836392 4/1952 Fed. Rep. of Germany.

Primary Examiner—Kyle L. Howell

[57] ABSTRACT

A stabbing apparatus for penetration of a living body wall, having a stabbing apparatus body provided with a sharp edge, a pressure sensor disposed on the peripheral surface thereof to sense the pressure to which the sensor is subjected when stabbing a living body wall, and an indicator responsive to the sensed pressure above a predetermined level, whereby the depth of penetration of the stabbing apparatus body with respect to the living body wall is indicated.

3 Claims, 11 Drawing Figures

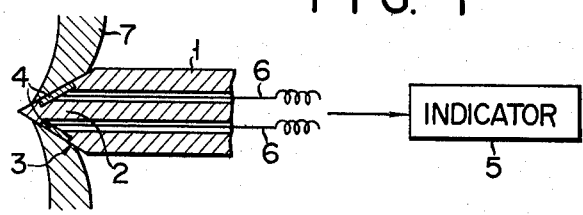
FIG. 1
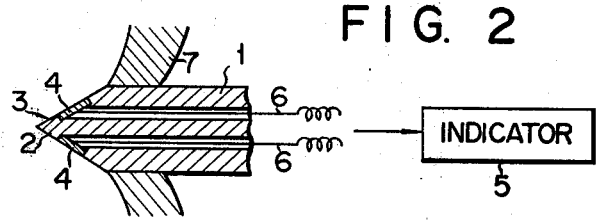
FIG. 2
FIG. 3   FIG. 4   FIG. 5
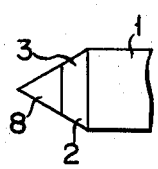 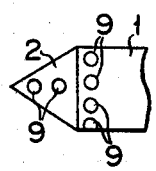 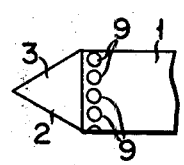
FIG. 6
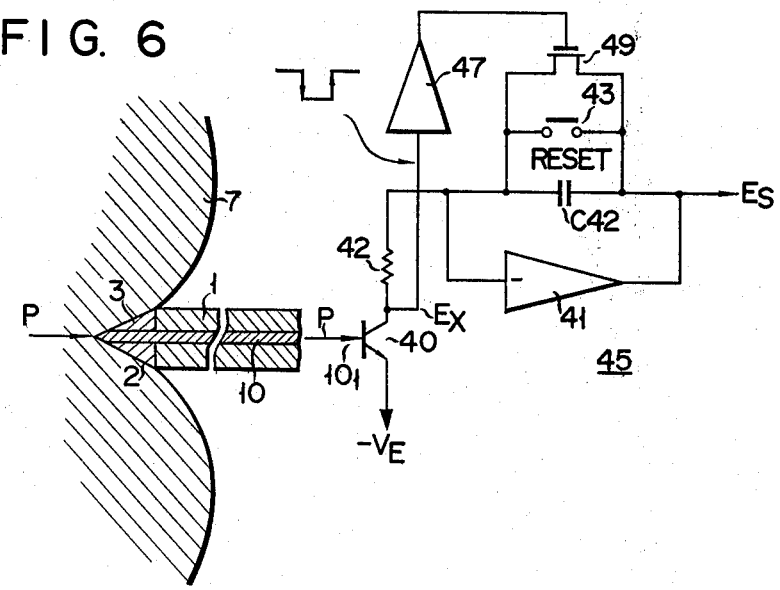

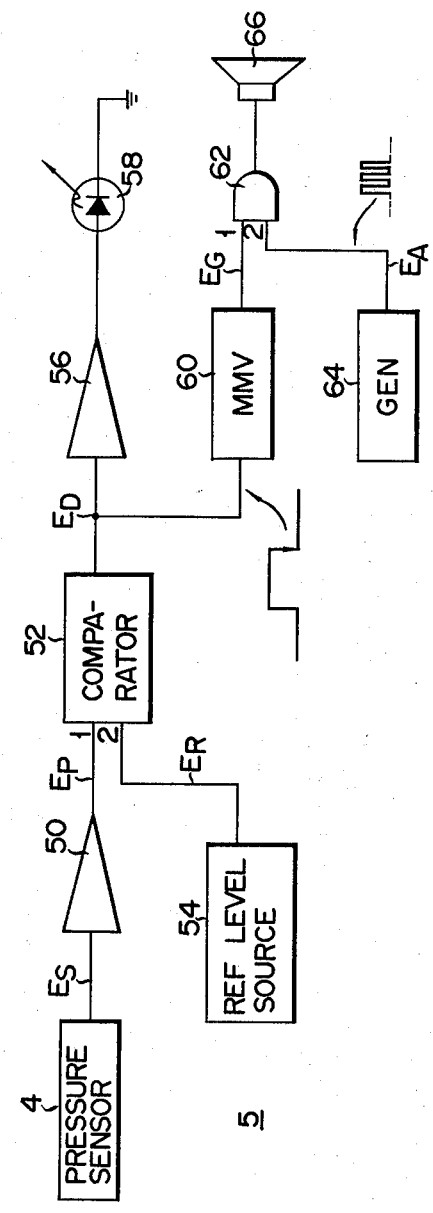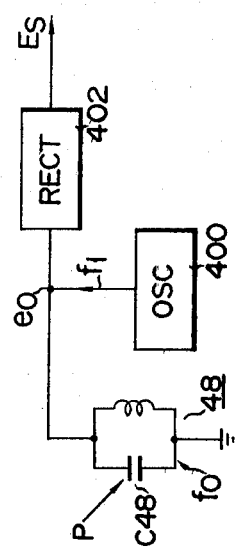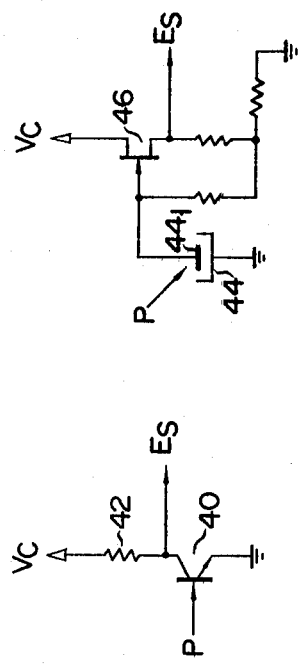
FIG. 7
FIG. 10
FIG. 9
FIG. 8

STABBING APPARATUS FOR DIAGNOSIS OF LIVING BODY

BACKGROUND OF THE INVENTION

This invention relates to a stabbing apparatus for diagnosis of living bodies such as a trocar for celioscopic examinations.

In spite of its very sharp edge, a trocar for celioscopic examinations will meet with strong resistance when it is stabbed into an abdominal wall. When the abdominal wall is once penetrated, however, the resitance will be suddenly removed, so that the apparatus will possibly damage some internal organs by continuing to exert the same force necessary for penetration. However, there has so far been taken no measure to counter such danger involved in the stabbing operation.

SUMMARY OF THE INVENTION

The object of this invention is to provide a stabbing apparatus for diagnosis of living bodies capable of safe stabbing without damaging any unrelated parts inside a living body wall, whereby the stabbing state can be perceived by means of a pressure sensor including a plurality of pressure sensor elements to sense a pressure to which it is subjected when stabbing the living body wall and an indicator connected to the pressure sensor elements to indicate the pressure condition.

According to the stabbing apparatus of the aforementioned construction, immediately when the tip end of the stabbing apparatus has pierced through the living body wall, the operator can be informed of such state by the indicator. Further, the operator can also know the depth of insertion of the stabbing apparatus in the living body wall. Then the operator may immediately reduce the force exerted on the apparatus and thereby minimize the possibility of damaging internal organs with the sharp edges of the apparatus. This also reduces the mental pressure on the operator which results from using prior art devices.

BRIEF DESCRIPTION OF THE DRAWING

FIG. 1 is a sectional view of an apparatus according to an embodiment of this invention showing a state immediately after the start of stabbing;

FIG. 2 is a sectional view of the same apparatus of FIG. 1 showing a pierced state;

FIGS. 3 to 5 are side views of the tip end portion of the apparatus showing various manners of arrangement of pressure sensors as shown in FIG. 1;

FIG. 6 shows a modification of the arrangement of the apparatus of FIG. 1 capable of measuring the stabbing depth;

FIG. 7 is a block diagram showing in detail the construction of an indicator as shown in FIG. 1;

FIGS. 8 to 10 show specific examples of the pressure element as shown in FIG. 1.

DETAILED DESCRIPTION OF THE PREFERRED EMBODIMENTS

Figure 11:
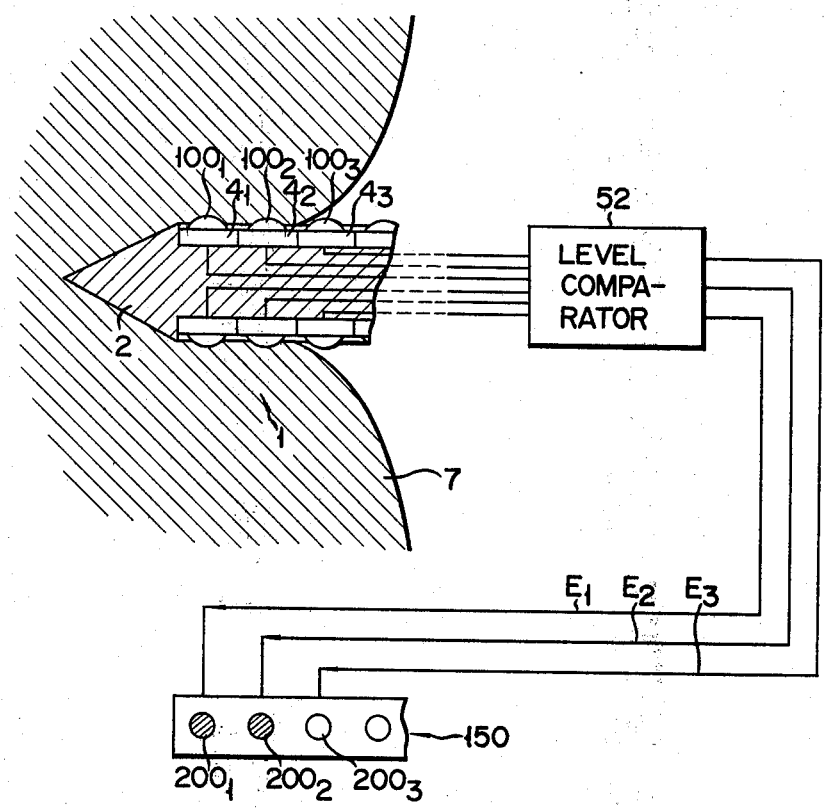
FIG. 11 shows a modification of the arrangement of the apparatus of FIG. 6 in which a pressure sensor array is used for the detection of the stabbing depth.

Now there will be described several preferred embodiments of this invention with reference to the accompanying drawings.

In FIG. 1, numeral 1 designates a stabbing apparatus body with a sharp conical edge 3 formed at a tip end portion 2 thereof. On the wall of the edge 3, there is provided a pressure sensor 4 to cause electrical changes such as those of resistance and capacitance. In stabbing the edge 3 into a living body wall, the pressure sensor 4 is subjected to a pressure, and senses the pressure to operate an indicator 5 as mentioned later. The pressure sensor 4 is connected to the indicator 5 by means of lead wires 6 passes through the stabbing apparatus body 1. If the apparatus body 1 is made of metal, it may be used for one of the lead wires 6. The indicator 5 is so designed as to give an audible or visual alarm in case of a sudden drop of the pressure to the pressure sensor 4. Naturally, the indicator 5 may raise both audible and visual alarms at the same time, or give an alarm by means of deflection of a pointer of meter. That is, it is necessary only that the operator be notified of the pressure condition by any suitable means.

In conducting a celiscopic examination, for example, the stabbing apparatus body 1 is covered with a sheathing (not shown), and is pressed against a living body wall 7, with the tip end portion 2 projected. First, in a state as shown in FIG. 1, that is, immediately before the apparatus body 1 pressed against the living body wall 7 pierces thereinto, the pressure sensor 4 is subjected to a high pressure. Then, in a state as shown in FIG. 2, that is, when the apparatus body 1 has pierced the living body wall 7, the pressure applied to the pressure sensor 4 is suddenly reduced. By this pressure change, the indicator 5 is actuated to give an alarm, whereby the operator realizes that the tip end portion 2 of the stabbing apparatus has pierced the living body wall 7. Thereafter, the stabbing apparatus can be inserted with a small force, so that the stabbing operation may be performed in safety without damaging any unrelated parts inside the living body wall 7. When the stabbing is accomplished, a normal celioscopic examination can be achieved by removing only the stabbing apparatus body 1 and inserting a celioscope (not shown) into the sheathing that is left in the living body.

The arrangement of the pressure sensor of this invention is not limited to the manner of the aforesaid embodiment, but may be such as shown in FIGS. 3 to 6. Namely, in FIG. 3, a chip of pressure sensor element 8 is embedded in the tip end of the stabbing apparatus body 1. In FIGS. 4 and 5, a plurality of pressure sensor elements 9 are arranged on the side face of the apparatus body 1 near the tip end thereof. In FIG. 6, a barlike pressure sensor device 10 is embedded in the stabbing apparatus body 1 along the axial direction thereof. At one end of the pressure sensor device 10, there is provided a pressure-sensitive transistor 40. When a local concentrated stress P is applied to the emitter-base junction of the transistor 40 by means of a pressure needle $10_1$, the transistor 40 supplies through a resistor 42 to a capacitor C42 a collector current proportional to the stress P. The capacitor C42 is connected in parallel with a phase-inverted amplifier 41 and a reset switch 43. The resistor 42, capacitor C42 and amplifier 41 form a mirror integrator 45, and a signal $E_S$ with a potential proportional to the accumulation value of the collector current of the transistor 40 appears at the output end of the amplifier 41. The capacitor C42 stores electric charges proportional to the accumulation value of the stress P. Representing the sum total of the pressures applied to the device 10, this accumulation value covers information corresponding to the stabbing depth of the stabbing apparatus body 1 pressed into the living body wall 7. That is, the stabbing depth may be determined from the level of the signal $E_S$. When the switch 43 is turned on, all the charges stored in the capacitor C42 are discharged for a subsequent stabbing operation.

The above-mentioned construction will be quite enough as long as the collector current of the transistor 40 is zero when the level of the stress P is at zero. However, if the collector current flows through the transistor 40 while the stress P is zero, the integration output of the integrator 45 or the signal $E_S$ will charge even though the apparatus body 1 is not being pressed into the living body wall 7. Therefore, in order to prevent such integration while the stress P is zero, there are provided an amplifier 47 and a switch transistor (MOS FET) 49. The FET 49, having its drain-source terminals connected in parallel with the capacitor C42, and the FET 49 is turned on when the stress P=0 to stop the integrating operation. When the stress P is applied (P≠0), a signal $E_X$ whose DC level is lowered in response to the application of the stress P appears at the collector of the transistor 40. The signal $E_X$ is amplified by the amplifier 47, and applied to the gate of the FET 49. Then, the FET 49 is turned off, and the integrating operation is started. That is, by the addition of the components 47 and 49, the integrating operation is allowed to be performed only while the stabbing apparatus body 1 is being pressed into the living body wall 7.

FIG. 7 shows a detailed arrangement of the indicator 5 as shown in FIG. 1. A pressure sensor 4 produces an electric signal $E_S$ corresponding to a given pressure. The signal $E_S$ is amplified by an amplifier 50 into a signal $E_P$ at a suitable level, which is applied to a first input terminal of a comparator 52. A second input terminal of the comparator 52 is supplied with a reference signal $E_R$ from a reference level source 54. The comparator 52 compares the levels of the signals $E_P$ and $E_R$ to deliver a detection signal $E_D$ if $E_P > E_R$, for example. The signal $E_D$ is supplied to an LED 58 through an amplifier 56. Namely, when the sensor 4 perceives a pressure above a predetermined level, the signal $E_D$ is produced to turn on the LED 58.

The signal $E_D$ is applied also to a monostable multivibrator (MMV) 60. The MMV 60 is triggered by a fall or disappearance of the signal $E_D$. Then, the MMV 60 supplies a gate signal $E_G$ at logic level "1" to a first input terminal of an AND gate 62 for a fixed time. This fixed time is determined in accordance with the time constant of the MMV 60 itself. A second input terminal of the AND gate 62 is supplied with an alarm signal $E_A$ of e.g. 1 kHz from an alarm generator 64. When the MMV 60 is triggered to turn the logic level of the gate signal $E_G$ to "1", the AND gate 62 is opened. Then, the alarm signal $E_A$ is supplied to a loudspeaker 66 via the AND gate 62. That is, the pressure applied to the sensor 4 is lowered below the aforesaid predetermined level after the sensor 4 has sensed the pressure above such level, the MMV 60 is triggered. Thus, the loudspeaker 66 produces an alarm sound to give notice that the stabbing apparatus body 1 or the edge 3 has pierced the abdominal wall of the living body.

FIGS. 8 to 10 show specific examples of the arrangement of the pressure sensor 4. FIG. 8 shows a case where a pressure-sensitive transistor 40 is used. When a local concentrated stress P is applied to the emitter-base junction of the transistor 40 by means of a pressure needle (not shown), the collector current of the transistor 40 changes. This current change leads to a change of a voltage drop appeared at a collector resistor 42. This voltage change provides the signal $E_S$.

FIG. 9 shows a case where an electric capacitor 44 is used. When the pressure P is applied to a charged film $44_1$ of the capacitor 44, the capacitance of the capacitor 44 changes. Then, accompanying the capacitance change, the level of the signal $E_S$ derived from the source of a FET 46 changes.

FIG. 10 shows a case where the resonance frequency of an LC resonance circuit 48 is varied by the pressure P. One electrode of a capacitor C48 forming the resonance circuit 48 is so designed as to be displaced by the pressure P. When the capacitance of the capacitor C48 is changed by such displacement, the resonance frequency $f_0$ of the resonance circuit 48 changes. The resonance circuit 48 is supplied with a high-frequency signal $e_0$ with frequency $f_1$ from an oscillator 400. The amplitude of the signal $e_0$ is at a maximum when $f_0$ is equal to $f_1$, and the amplitude is descreasing as $|f_0-f_1|$ increases. In other words, the amplitude of the signal $e_0$ changes in accordance with the pressure P. The signal $E_S$ may be obtained by rectifying the signal $e_0$ by means of a rectifier 402.

FIG. 11 shows a modification of the apparatus of FIG. 6, in which a pressure sensor array is used for the detection of the stabbing depth. That is, a plurality of pressure sensor elements $4i$ (i=1, 2, 3 ...) are arranged in an array along the peripheral surface of the stabbing apparatus body 1. These elements $4i$ are successively pressed by the living body wall 7 through projected portions $100i$ (i=1, 2, 3 ...). The outputs of the elements $4i$ are severally applied to the input of a level comparator 52. The comparator 52 produces signals Ei (i=1, 2, 3 ...) in accordance with the pressure outputs from the elements $4i$. FIG. 11 shows a state in which the elements $4_1$ and $4_2$ are pressed by the living body wall 7. When the elements $4_1$ and $4_2$ are pressed, indicator elements or LED's $200_1$ and $200_2$ arranged on an LED array 150 are turned on. As the stabbing apparatus body 1 is inserted into the living body wall 7, a bar of the lighted LED's on the LED array 150 extends. On the other hand, when the body 1 has pierced through the living body wall 7 to release the element $4_1$ from the press, the LED $200_1$ is turned off. Thus, according to the apparatus of FIG. 11, there may be indicated the time when the apparatus body 1 has pierced through the living body wall 7, as well as the depth of insertion of the body 1 in the living body wall 7.

Although specific constructions have been illustrated and described herein, it is not intended that the invention be limited to the elements, devices and/or circuit constructions disclosed. One skilled in the art will recognize that the particular elements, devices or subcircuits may be used or combined without departing from the scope and spirit of the invention. For example, the elements $4i$ and portions $100i$ show in FIG. 11 may be arranged not only in the peripheral surface of the body 1 but also in the surface of the tip end portion 2 or edge 3. Further, the FIG. 7 construction may be combined with the FIG. 11 or FIG. 6 arrangement for indicating that the body 1 has been pierced into the abdominal wall, as well as for indicating the stabbing depth.

What is claimed is:

1. A stabbing apparatus for penetration of a living body wall comprising:
   a stabbing apparatus body having a sharp edge;
   a plurality of pressure sensor elements axially disposed on the peripheral surface of said stabbing apparatus body to sense in succession the pressure to which each said sensor is subjected during penetration of a living body wall; and means connected to said sensor elements for detecting the pressure above a predetermined level exerted upon each respective sensor element, including separate indicator means responsive to said pressure for each successive axially disposed sensor, whereby the depth of penetration of said stabbing apparatus body with respect to said living body wall is indicated.

2. A stabbing apparatus according to claim 1, wherein said indicator means includes a reference level source to provide a reference signal representing said predetermined level, a comparator comparing a first signal corresponding to the sensed pressure with said reference signal and delivering a second signal when said first signal becomes higher or lower than said reference signal and an indicator device to indicate stabbing of said edge into said living body wall by means of said signal.

3. A stabbing apparatus according to claim 2 further comprising a monostable multivibrator triggered by disappearance of said second signal to produce a third signal for a fixed time, an alarm generator to provide a fourth signal for an alarm operation, a gate circuit to provide the logical product of said third and fourth signals and an alarm device to perform the alarm operation when the logic levels of said third and fourth signals both become "1" in said gate circuit.

* * * * *